US00PP35436P3

(12) United States Plant Patent
Seemüller

(10) Patent No.: US PP35,436 P3
(45) Date of Patent: Oct. 24, 2023

(54) APPLE TREE ROOTSTOCK NAMED 'D2212'

(50) Latin Name: ***Malus* Mill**
Varietal Denomination: D2212

(71) Applicant: Bundesrepublik Deutschland vertreten durch das Julius Kühn-Institut, Quedlinburg (DE)

(72) Inventor: Erich Seemüller, Dossenheim (DE)

(73) Assignee: Bundesrepublik Deutschland vertreten durch das Julius Kühn-Institut, Quedlinburg (DE)

( * ) Notice: Subject to any disclaimer, the term of this patent is extended or adjusted under 35 U.S.C. 154(b) by 0 days.

(21) Appl. No.: 17/963,246

(22) Filed: Oct. 11, 2022

(65) Prior Publication Data

US 2023/0157189 P1 May 18, 2023

Related U.S. Application Data

(60) Provisional application No. 63/361,051, filed on Nov. 18, 2021.

(51) Int. Cl.
*A01H 5/08* (2018.01)
*A01H 6/74* (2018.01)
*A01H 5/06* (2018.01)

(52) U.S. Cl.
USPC ..... Plt./174
CPC ..... *A01H 6/7418* (2018.05); *A01H 5/06* (2013.01)

(58) Field of Classification Search
USPC ..... Plt./174
CPC ..... A01H 5/0875
See application file for complete search history.

(56) References Cited

PUBLICATIONS

David C. Ferree; HortScience; Performance of Eight Apomictic Selections as Apple Rootstocks; 33(4):641-643; 1998.*

* cited by examiner

*Primary Examiner* — Kent L Bell
(74) *Attorney, Agent, or Firm* — The Webb Law Firm

(57) ABSTRACT

A new and distinct variety of apple tree rootstock that exhibits compatibility with numerous apple varieties and resistance to *Candidatus Phytoplasma mali* and *Athelia rolfsii.*

3 Drawing Sheets

Botanical classification: *Malus* Mill.
Varietal denomination: 'D2212'.

BACKGROUND OF THE NEW PLANT

The present invention comprises a new and distinct variety of apple tree that is solely used as a rootstock and known by the varietal name 'D2212'. The new variety was developed by the breeder as part of a planned breeding program in Ahrensburg, Germany. The purposes of the breeding program were to obtain rootstocks with resistance to *Candidatus Phytoplasma mali* and with reduced plant vigor. 'D2212' is the result of open pollination of an unpatented variety of *M. domestica* x *M. sieboldii* named 'Laxton's Superb' (female parent) occurring before 1994, but with the year not certain. As a result, the exact male parent is unknown. The new variety was selected and first asexually reproduced by in-vitro propagation in Stuttgart, Germany in 2007.

When compared to unpatented *Malus* Mill. varieties referred to as PJ-P 21 (APU 85) and M 25 (APU 29), 'D2212' has crenate leaf blade margin incisions, while the comparison varieties have serrate leaf blade margin incisions. Further, 'D2212' has weak pubescence on the lower side of its leaf blades, while M 25 (APU 29) has strong pubescence on the lower side of its leaf blades. Also, resistance to *Candidatus Phytoplasma mali* and *Athelia rolfsii* are distinguishing characteristics of the new variety from other apple tree varieties known to the breeder.

The new variety has not been evaluated under all possible environmental conditions. The phenotype may vary with variations in environment without a change in the genotype of the plant. The new variety has been trial and field tested and has been found to retain its distinctive characteristics and remain true to type through successive asexual propagations.

DESCRIPTION OF THE DRAWINGS

The accompanying photographic drawings illustrate the new variety with the color being as nearly true as possible with color illustrations of this type.

DETAILED BOTANICAL DESCRIPTION

Figure 1:
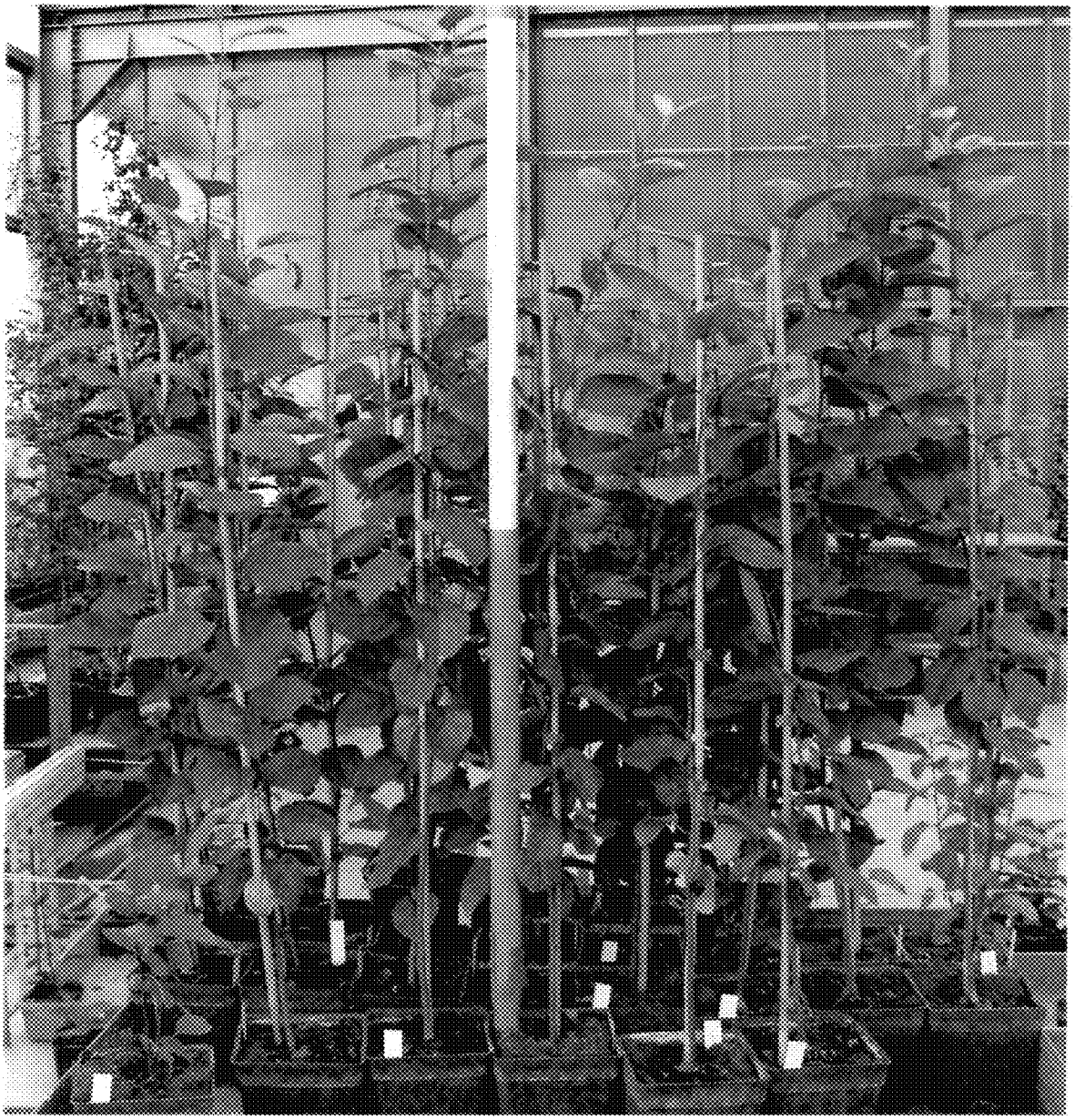
FIG. 1 illustrates multiple plants of the new variety at approximately 1 year of age.
Figure 2:
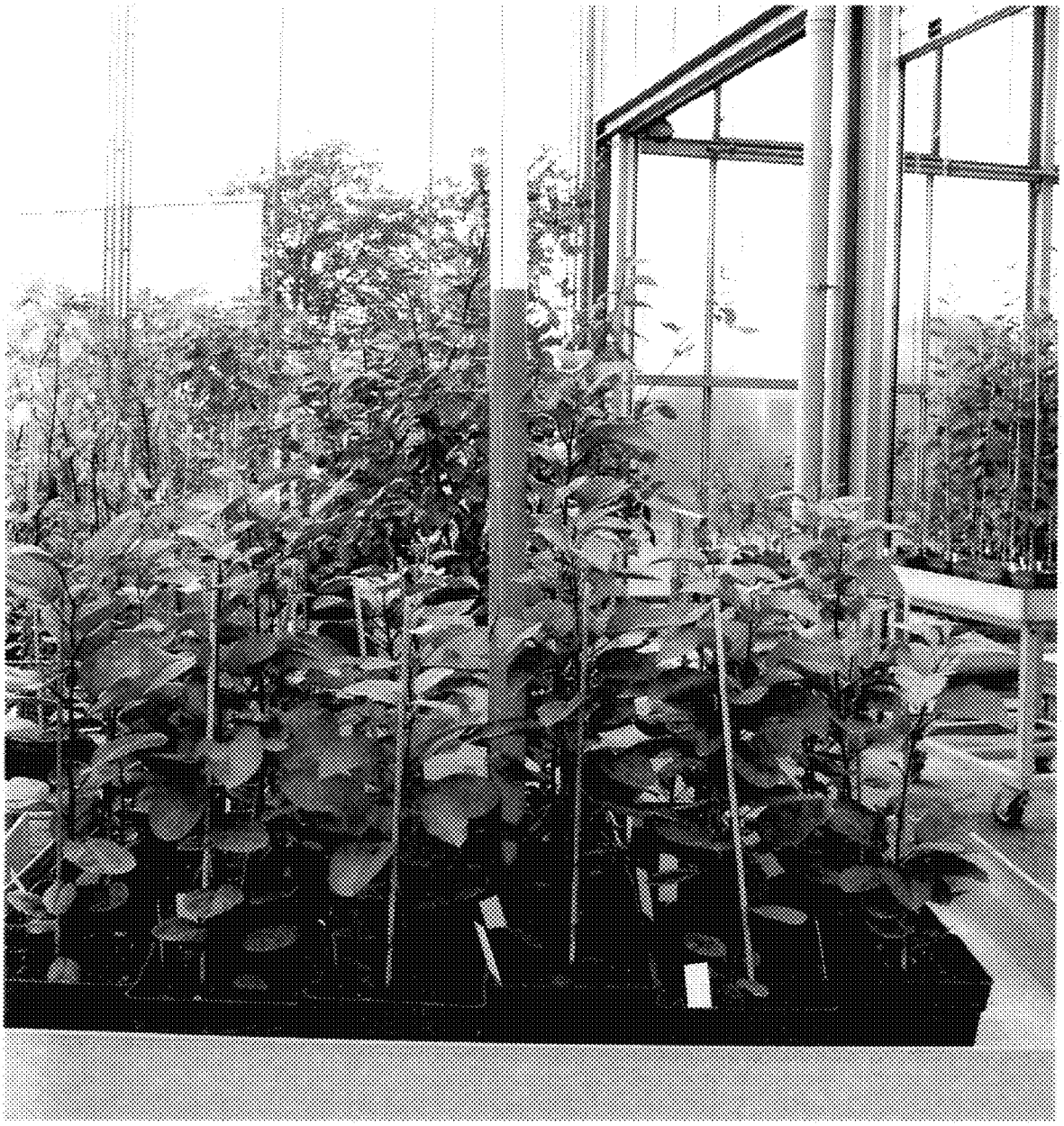
FIG. 2 illustrates multiple young plants of the new variety.
Figure 3:
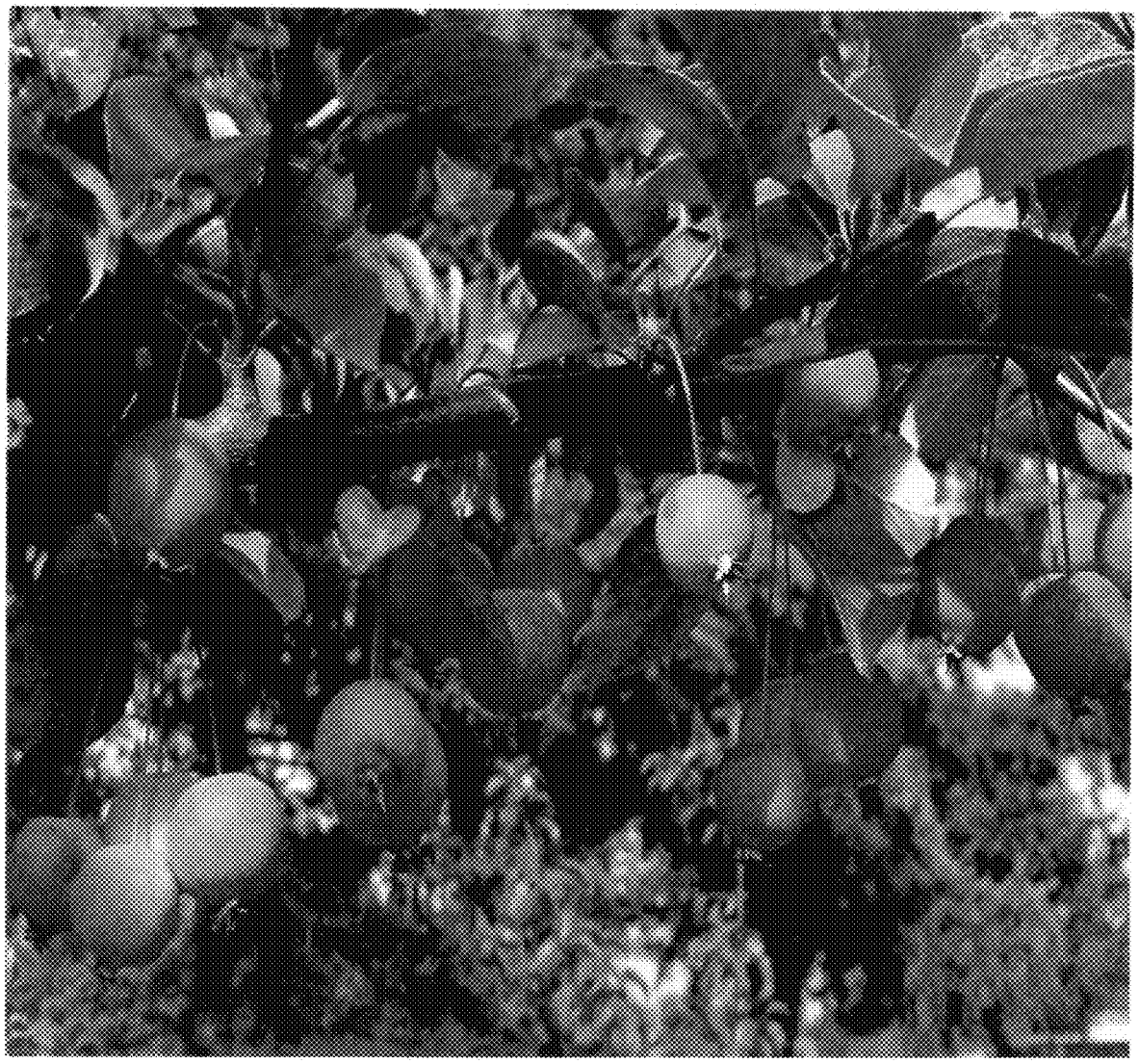
FIG. 3 illustrates the new variety at 7 years of age with fruits thereon.

The following detailed description sets forth the characteristics of the new variety at approximately 1 year of age and on a mother plant at 7 years of age. The data which defines these characteristics were collected as a result of asexual reproductions carried out in Rheinstetten, Germany on potted plants under standard growing conditions and taken under natural light. Where applicable, color descriptions are provided using X11 Color Names and their corresponding HEX Color Codes, accessed in August of 2022 via www.farbtabelle.de/de/farbtabelle.htm.

ROOTSTOCK

Height: 150.0 cm.
Thickness: 12.0 mm.
Vigor: Medium.
Tree habit: Upright and straight growth.
Form: Spindle.
Use: Solely as a rootstock.
Multiplication ability:
*Layering*.—Not determined to date.
*Hardwood cuttings*.—Very difficult.
*Softwood cuttings*.—Possible, but with low yields.
Pathogen resistance: Resistant to *Candidatus Phytoplasma mali* and *Athelia rolfsii*.
Pest resistance/susceptibility: Not observed to date.
Rootstock performance:
*Root sprouts* (*suckering*).—None.
*Anchorage*.—Stable in the ground.
*Compatibility*.—Compatible with all varieties known to the inventor.
*Vigor*.—Medium to strong.
Shoot:
*Diameter*.—Thick at midpoint, but difficult to measure as very dependent on age and soil conditions.
*Internode length*.—Medium to long; average of 2.75 cm.
*Texture*.—Pubescence present on upper half of shoot.
*Glossiness of bark*.—Medium to strong.
*Color*.—Red, HEX #973307 on sunny side.
*Growing tip color*.—Maroon, HEX #800000.
Buds:
*Position*.—Adpressed relative to axis.
*Size*.—Length from 6.0-10.0 mm and width from 4.0-5.0 mm.
*Shape of tip*.—Pointed.
*Support size*.—Small to medium.
Lenticels:
*Quantity*.—Average; approximately 10 lenticels per 2.0 cm shoot length.
*Length*.—Medium to long; average of 1.0 mm.
*Shape*.—Elliptic.
*Color*.—Burlywood 1, HEX #ffd39b.
Petiole:
*Shape*.—Straight.
*Length*.—2.0 cm; 3.5 length of blade to length of petiole ratio.
*Diameter*.—0.15 cm.
*Color*.—Upper surface is sienna, HEX #a0522d; lower surface is red3, HEX #cd0000.
Leaves:
*Arrangement*.—Alternate, spiral.
*Length*.—From 6.5 to 7.0 cm.
*Width*.—From 5.0 to 6.0 cm.
*Form*.—Generally, elliptic-oval. Lower base leaves are often triangular with basal lobes.
*Profile*.—Concave in cross section.
*Apex*.—Pointed.
*Base*.—Orbicular-obtuse.
*Margin*.—Serrate.
*Texture*.—Upper surface is smooth; lower surface has weak pubescence present.
*Color*.—Upper surface is OliveDrab4, HEX #698b22; lower surface is DarkOliveGreen3, HEX #a2cd5a; young leaves have bronze, HEX #cd7f32 anthocyanin coloration present.
*Venation*.—Type: Pinnate, alternate. Color: On expanding leaves, slightly reddish with very weak to weak anthocyanin coloration present, both colors being tomato2, HEX #ee5c42.
Flower buds:
*Pedicel*.—Length: 4.5 cm. Diameter: 1.0 mm. Color: Tan4, HEX #8b5a2b.
*Bud*.—Shape: Obtuse, with a blunt tip. Length: 1.0 cm. Width: 4.0 mm. Color: HotPink, HEX #ff69b4.
Flowers:
*Bloom timing*.—From April 23 to May 8 in Rheinstetten, Germany.
*Blooming period*.—Two weeks.
*Number of flowers per cluster*.—4 to 6.
*Fragrance*.—Weakly sweet.
*Petals*.—Number: 5. Length: 2.5 cm. Width: 1.7 cm. Shape: Orbicular. Apex: Round. Base: Round and tapering to the center of the base. Margin: Entire. Texture: Smooth.
*Color*.—When opening: Upper surface: Pink1, HEX #eea968. Lower surface: MistyRose, HEX #ffe4el. Fully opened: Upper surface: White, HEX #ffffff. Lower surface: Light Pink1, #ffaeb9.
*Sepals*.—Shape: Rhomboid. Apex: Triangular, long, and pointed. Margin: Entire. Texture: Smooth. Length: 4.0 to 5.0 mm. Width: 1.0 mm. Color: Upper surface: OliveDrab4, HEX #698b22. Lower surface: OliveDrab3, HEX #9acd32.
Reproductive organs:
*Stamens*.—Number (per flower): 12. Filament length: 3.0 mm.
*Anthers*.—Shape: Round. Length: 1.0 mm. Color: Gold3, HEX #cdad00.
*Pollen*.—Color: Gold3, HEX #cdad00. Amount: Scarce.
*Pistils*.—Average number: 4. Length: 2.4 cm.
*Style*.—Length: 7.0 mm. Color: Cornsilk3, HEX #cdc8b1.
*Stigma*.—Shape: Round. Color: NavajoWhite3, HEX #cdb38b.
Fruit: Not observed to date.

I claim:

1. A new and distinct variety of apple tree rootstock named ‘D2212’, as is herein illustrated and described.

* * * * *